(12) United States Patent
Kaiser

(10) Patent No.: US 7,182,845 B2
(45) Date of Patent: Feb. 27, 2007

(54) ELECTROCHEMICAL SENSING CIRCUIT HAVING HIGH DYNAMIC RANGE

(75) Inventor: Timothy D. Kaiser, Plain City, OH (US)

(73) Assignee: Ranco Incorporated of Delaware, Wilmington, DE (US)

( * ) Notice: Subject to any disclaimer, the term of this patent is extended or adjusted under 35 U.S.C. 154(b) by 320 days.

(21) Appl. No.: 10/966,822

(22) Filed: Oct. 15, 2004

(65) Prior Publication Data

US 2006/0081470 A1    Apr. 20, 2006

(51) Int. Cl.
*G01N 27/416*    (2006.01)
(52) U.S. Cl. ...................... 204/406; 204/431
(58) Field of Classification Search ............... 204/406, 204/403.01, 403.15, 416, 431
See application file for complete search history.

(56) References Cited

U.S. PATENT DOCUMENTS 4,642,172 A * 2/1987 Fruhwald .................. 204/229.1
6,277,255 B1   8/2001 Green et al.

\* cited by examiner

*Primary Examiner*—Alex Noguerola
(74) *Attorney, Agent, or Firm*—Reinhart Boerner Van Deuren P.C.

(57) ABSTRACT

An electronic sensing circuit for an electrochemical gas sensor cell providing high dynamic range is described. The electronic circuit utilizes an amplifier with a resistive feedback element to provide high sensitivity linear sensing of low detected gas concentrations. The electronic circuit also provides the ability to source sufficient current to prevent the electrochemical gas sensor cell from becoming biased under very high gas concentration conditions. This operation is enabled by adding a non-linear element in the feedback path of the amplifier, which non-linear element begins to conduct during the high gas concentration conditions.

20 Claims, 2 Drawing Sheets

ELECTROCHEMICAL SENSING CIRCUIT HAVING HIGH DYNAMIC RANGE

FIELD OF THE INVENTION

The present invention relates generally to electrochemical sensing circuits and more particularly to electrical circuits which sense cell current flow from a three terminal electrochemical cell.

BACKGROUND OF THE INVENTION

Three terminal electrochemical cells are used for a variety of gas monitors. These monitors comprise a cell in which a gas to be analyzed is introduced and three spaced apart electrodes. The three electrodes comprise a main pair across which the cell current is generated and a reference electrode which enables a potential at a predetermined point in the cell electrolyte measured. The cell current is proportional to the concentration of the compound or element being sensed by the cell, which may, for example, be carbon monoxide.

Known three-terminal electrochemical cells can be stabilized using the circuit shown in FIG. 1. In order to stabilize the cell, the "working" and "reference" electrodes, labeled "W" and "R" respectively must be brought to the same electrical potential. No current is taken from the reference electrode. Instead, current is injected into the counter electrode, labeled "C", by the amplifier A1 until both the reference and working electrodes, R and W respectively, are the same potential. The current which flows in both the counter and working electrodes is the cell current. Due to the internal operation of the cell, this is proportional to the concentration of the compound being sensed by the cell.

Referring to FIG. 1, the amplifier A1 maintains the reference electrode at 0V by feeding back current to the counter electrode. Amplifier A2 maintains the working electrode at 0V, since the input of amplifier A2 is at 0V. The cell current is driven by amplifier A1 but is sensed by amplifier A2, because the cell current passes through resistor R2 to develop the voltage V out.

A disadvantage of this prior known circuit shown in FIG. 1 is that it is prone to oscillation because the virtual earth impedance of each amplifier appears as part of a feedback path of the other amplifier. This can lead to oscillation at high frequencies where the virtual earth impedances are not well defined. A further disadvantage is that, whereas Vout is normally positive when gas is being sensed, the counter electrode charges negatively, requiring the output of amplifier A1 to go negative. Therefore the circuit shown in FIG. 1 requires both positive and negative supplies (shown as +V and −V).

To overcome these disadvantages and to allow the detector and associated circuitry to be operated from a single battery source, the circuit of FIG. 2 was developed. This circuit is described in U.S. Pat. No. 6,277,255, entitled Electrochemical Sensing Circuits, to Green, et al. This patent describes an electrochemical cell having a working electrode, a counter electrode and a reference electrode in an electrolyte as shown in FIG. 2. The cell is constructed such that in use, when a gas to be analyzed is introduced into the cell, a current flows between the counter electrode and the working electrode. A potential at a position in the electrolyte is sensed by the reference electrode. The circuit also includes a power supply for applying an offset voltage to the counter electrode relative to the working electrode. An amplifier circuit monitors the voltage difference between the reference electrode and the working electrode. This amplifier circuit feeds back a current to the working electrode through a feed back loop in order to maintain the working electrode at substantially the same potential as the reference electrode. The current fed back by the amplifier to the working electrode is monitored as a measure of the cell current flowing between the working electrode and the counter electrode. The current is monitored as a voltage across the resistor in the feed back loop indicated as Vout.

While this circuit overcame the shortcomings of the prior monitoring circuits and allowed usage of a single polarity DC source such as a battery, emerging agency standards, e.g. UL 2034 and EN 50291, are placing increasing demands on the electrochemical cell sensing circuitry. Specifically, since electrochemical gas sensors are current output devices, as the gas of interest is introduced into the sensing cell, e.g., carbon monoxide (CO), the amount of current produced by the cell increases. To allow the sensor to work properly, the output current must always be maintained at a desired bias condition. As with the circuitry described above, for products such as CO detectors, the output current is usually converted into a voltage by an amplifier. This voltage can then be read by a microprocessor. While the microprocessor can read this output voltage in a variety of ways, one of the most common methods is to supply the voltage to an analog to digital (A/D) converter.

In order to meet the agency standards, the circuitry used in a typical CO detector must be able to respond to very low levels of CO, in the 10's of parts per million (ppm) concentration levels. However, the typical carbon monoxide detector must also react, albeit in a faster time, to CO concentrations in the 1000's of ppm exposure. Since most microprocessors utilize a A/D converters that are 8 or 10 bits, the resolution available is either 256 or 1024 possible concentrations, respectively. In many applications the A/D resolution in and of itself does not impose too much of a limitation despite the wide range of input conditions that the detector must be able to sense accurately. Instead, because many such carbon monoxide detectors are battery powered devices, the number and magnitude of the power supply voltages powering the electronics is the limiting factor.

In the simplest of implementations, the current to voltage converter and the microprocessor are both powered by the same power supply. For practical purposes in a consumer device, e.g., to conserve battery life, this supply is typically 3.3 volts DC. With such a limitation, the problem is to allow the amplifier, e.g., a transimpedance amplifier (TIA) to convert the sensor output current for low level exposures to CO to be read by the microprocessor, and still allow the amplifier to have enough capacity such that it can source the current produced by the electrochemical cell at the tens of thousands of ppm exposure to CO gas for over exposure conditions. If the sensing electronics are unable to source this higher current, the sensor typically becomes biased and is unable to recover quickly from such high concentration exposures.

There exists, therefore, a need in the art for an electronic circuit having a high dynamic range such that it is capable of accurately monitoring the output of an electrochemical gas sensor cell that responds to gas concentrations in the 10's of ppm through the tens of thousands of ppm of CO concentration. More particularly, there is a need in the art for an amplifier configuration that allows maximum sensitivity while allowing for sensor recovery to very high gas concentrations for an electrochemical sensor.

BRIEF SUMMARY OF THE INVENTION

In view of the above, it is an object of the present invention to provide a new and improved electronic circuit that senses cell current flow from a three terminal electrochemical gas sensor cell that overcomes the above problems existing in the art. More particularly, it is an object of the present invention to provide a new and improved amplifier configuration that allows high sensitivity to the electrochemical gas sensor cell output during periods of low gas concentration while allowing for rapid sensor recovery when the electrochemical gas sensor is exposed to very high gas concentrations. Specifically, it is an object of the present invention to provide a new and improved electronic circuit for sensing the output of a electrochemical gas sensor that has a very high dynamic range such that operation of the hazardous condition detector in which it is utilized may meet agency standards.

In the electronic circuit of one embodiment to the present invention the circuitry provides high resolution of measurements while limiting the power supply needed for high concentrations of gas. In this embodiment, this is achieved by utilizing a non-linear element in the feedback of an amplifier. As such, at low levels of gas concentration the output signal is defined by the feedback resistance. At the point that the non-linear element begins to conduct, the gas concentration is high and the area of interest for linear signals has passed. Under such conditions the amplifier circuitry is still able to maintain the current sourced by the electrochemical gas sensor with a much smaller power supply.

In a preferred embodiment of the present invention, the electronic sensing circuitry utilizes a resistive feedback from the output of an amplifier to the working electrode of a three terminal electrochemical gas sensor cell. In addition to this feedback resistor, a pair of series connected transistors are coupled in parallel to the feedback resistor. These two transistors act as a single diode in that they do not conduct in negative polarity. However, in positive polarity there exists a region of potential in which no current will flow through these devices, i.e., the feedback resistor is the only element through which current may flow. If the voltage potential increases beyond the turn on voltage of the transistors, they will begin to conduct current. This conduction will allow the amplifier to maintain the current through the electrochemical sensor without requiring additional voltage potential across the feedback resistor. This provides an increased dynamic range of the amplifier while still utilizing the low voltage supply of the battery.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE PREFERRED EMBODIMENT

Figure 1:
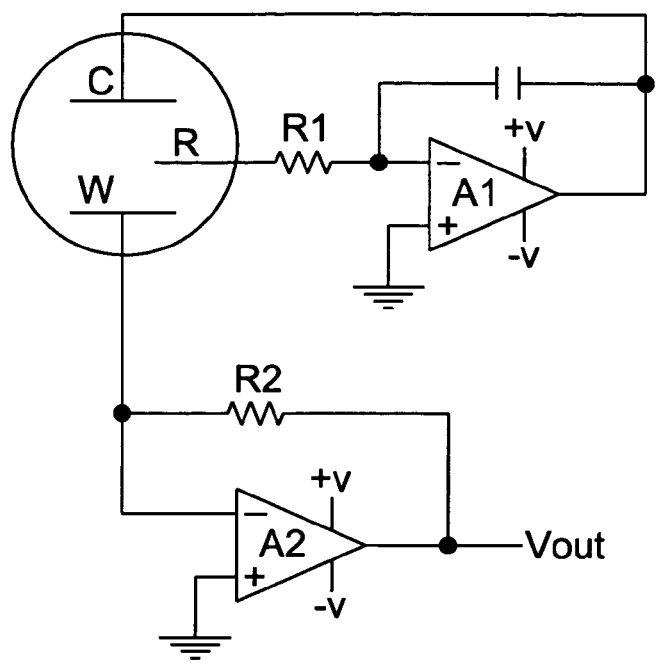
FIG. 1 is a simplified single line circuit schematic of a prior electrochemical sensing circuit.
Figure 2:
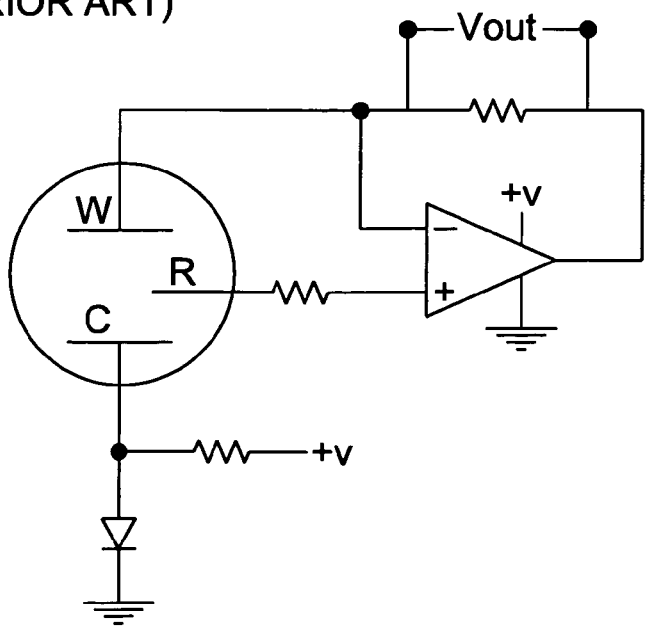
FIG. 2 is a simplified single line circuit schematic of an improved prior electrochemical sensing circuit.
Figure 3:
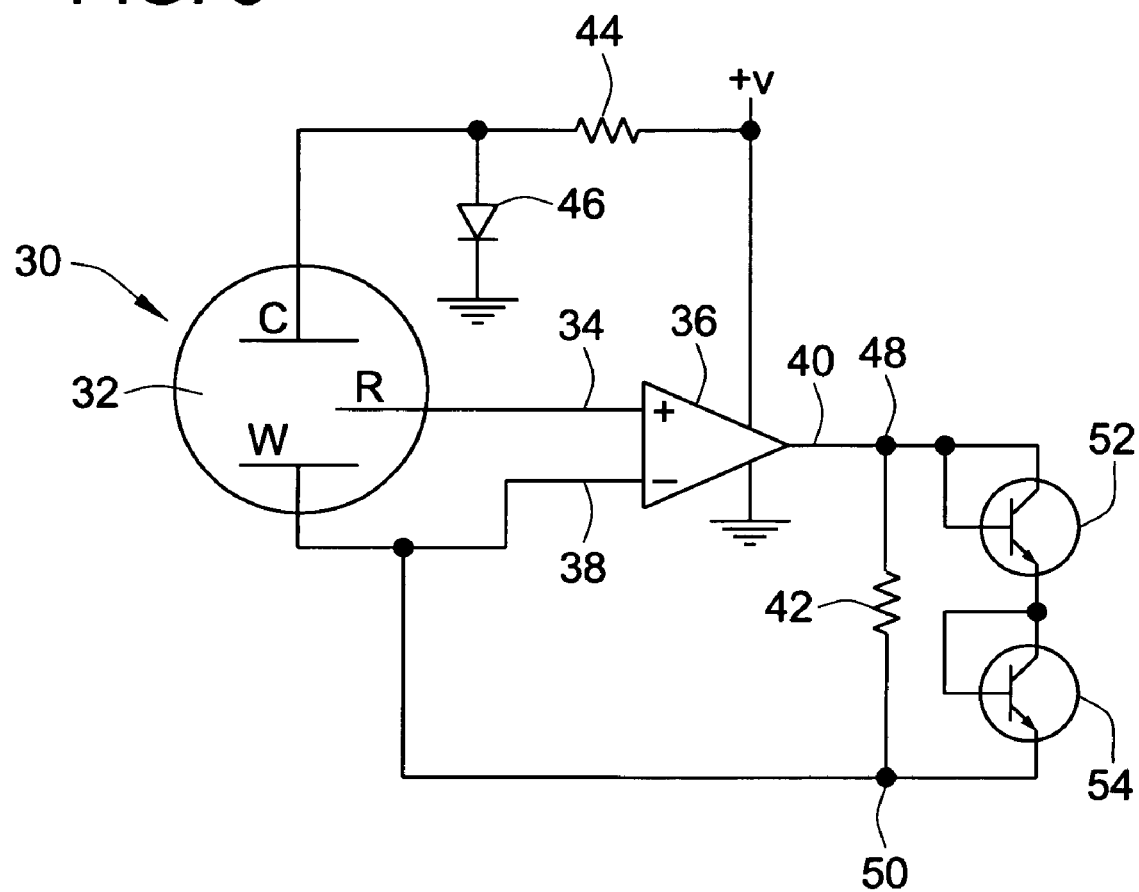
FIG. 3 is a simplified single line circuit schematic of an electrochemical sensing circuit constructed in accordance with the teachings of the present invention.

Referring to FIG. 3, the electrochemical cell 30 is of conventional construction and comprises a chamber, or cavity 32 into which a gas to be monitored is introduced. Three spaced electrodes W, C, R are located in the cavity 32. Electrode R constitutes a reference electrode and is connected to an input 34 of an operational amplifier 36. A second input 38 of amplifier 36 is connected to the electrode W. The output 40 of the amplifier 36 is connected to electrode W through a feedback loop which includes resistor 42. The counter electrode, C, is connected to a reference voltage generated by resistor 44 and diode 46 which is connected to the circuit ground.

The amplifier 36 feeds back current through resistor 42 to maintain the working and reference electrodes, W and R respectively, at the same potential.

When gas is sensed by the cell 30, the output of amplifier 36 goes positive to deliver a positive current into the working electrode W, and at the same time, the electrode W charges positive with respect to the counter electrode C. These two effects ensure that the output 40 of amplifier 36 remains positive relative to the circuit ground at all times.

The voltage across resistor 42 is an accurate output which is proportional to gas concentration in the cell 30. If the +V supply is provided by an isolated battery (not shown), the terminals 48, 50 of the resistor 42 can be taken as the output with one terminal connected to an external isolated ground. Where accuracy is less important, it may be sufficient to sense the output of amplifier 36 relative to the circuit ground, but the output voltage of amplifier 36 includes a component due to the offset voltage between the working electrode, W, and the counter electrode C. The offset is normally a very small fraction of a volt.

The offset voltage on the counter electrode, C, is generated by resistor 44 and diode 46 and protects those cells which would otherwise have an in-built tendency for the counter electrode to be positive relative to the working electrode. The offset voltage also allows for exposure to gases which would otherwise spuriously provoke a reverse response from the cell. If the cell is designed to have an inbuilt positive bias from the counter electrode, C, to the working electrode, W, it may not be necessary to impose an offset voltage on counter electrode C.

In addition to the resistor 42, the circuit of the present invention also utilizes a non-linear element in the feedback path of amplifier 36. Specifically, in one embodiment of the present invention the non-linear element may be implemented as a pair of transistors 52, 54 coupled in parallel to resistor 42. However, those skilled in the art will recognize that a single transistor may be utilized depending on circuit parameters. This non-linear element operates such that it is non-conducting at low levels of signals corresponding to low detected gas concentrations. As such, the voltage at terminals 48, 50 is defined solely by the output current multiplied by the resistance 42. However, as the concentration of detected gas increases, a larger current will begin to flow. As the voltage generated across feedback resistor 42 increases due to this increasing current, the non-linear elements begin to conduct, effectively reducing the feedback path resistance. The amplifier is then able to maintain the current through the electrochemical sensor 30 while still utilizing only the small power supply sourced from the battery.

In the environment of the present invention illustrated in FIG. 3 the two transistors 52, 54 may be thought of as a single diode that, in the negative polarity, do not conduct. However, in the positive polarity these transistors 52, 54 may begin to conduct. That is, in the positive polarity there is a region of potential across resistor 42 in which the transistors 52, 54 do not conduct. This is the linear sensing region of the circuit. However, as the potential across resistor 42 increases due to the sensing of a high concentration of detected gas, the area of interest for linear sensing has passed. In other words, at such high concentrations the carbon monoxide detector will have already sounded its alarm. However, unlike prior circuits the circuits of the present invention will provide rapid sensor recovery once the very high gas concentration is no longer present. That is, once the very high gas concentration of detected gas has cleared, the sensor will rapidly return to its linear sensing operation. Since the amplifier 36 is able to source enough current during the very high detected gas concentration, the sensor does not become biased, which typically results in the slow recovery once the concentration has cleared. In the circuit of FIG. 3, once the voltage potential across resistor 42 increases beyond the turn on voltage of the transistors 52, 54, these transistors will enter their conduction phase to allow additional current to flow therethrough without an additional voltage potential needed across the resistor 42. This provides the increased dynamic range of the amplifier while enabling the use of the low supply voltage, e.g., a battery.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A sensing circuit for an electrochemical sensing cell having a counter electrode, a reference electrode, and a working electrode, the electrochemical sensing cell generating a current flow between the counter electrode and the working electrode upon exposure to a gas, comprising an amplifier having a non-inverting input adapted to be coupled to the reference electrode of the electrochemical sensing cell, and an inverting input adapted to be coupled to the working electrode of the electrochemical sensing cell, the amplifier further including a resistor in a feed back path from the output of the amplifier to the inverting input of the amplifier, and a non-linear element coupled in parallel with the resistor, and wherein a voltage generated across the resistor provides an indication of the current flow between the counter electrode and the working electrode.

2. The sensing circuit of claim 1, wherein the non-linear element comprises at least one transistor.

3. The sensing circuit of claim 2, wherein the non-linear element comprises two series connected transistors.

4. The sensing circuit of claim 3, wherein the series connected transistors are configured as voltage followers.

5. The sensing circuit of claim 1, wherein the non-linear element does not conduct when the polarity of the output of the amplifier is negative.

6. The sensing circuit of claim 1, wherein the non-linear element does not conduct below a predetermined voltage across the resistor.

7. The sensing circuit of claim 6, wherein a voltage developed across the resistor provides a linear indication of the current flow between the counter electrode and the working electrode when the non-linear element is not conducting.

8. The sensing circuit of claim 1, wherein the non-linear element begins to conduct at a predetermined voltage across the resistor.

9. The sensing circuit of claim 8, wherein a voltage developed across the resistor no longer provides a linear indication of the current flow between the counter electrode and the working electrode when the non-linear element is conducting, the amplifier instead sourcing current to the working electrode to prevent the electrochemical sensor cell from becoming biased due to a high concentration of detected gas.

10. The sensing circuit of claim 1, wherein the amplifier is powered by a direct current source.

11. The sensing circuit of claim 10, wherein the direct current source is operatively coupled to the counter electrode of the electrochemical sensing cell to apply an off-set thereto.

12. A hazardous gas sensor for use in a battery powered hazardous condition detector, comprising:

an electrochemical sensing cell having a counter electrode, a reference electrode, and a working electrode, the counter electrode operatively coupled to the battery, the electrochemical sensing cell containing an electrolyte to facilitate a current flow between the counter electrode and the working electrode upon exposure to the hazardous gas;

an amplifier having a non-inverting input coupled to the reference electrode of the electrochemical sensing cell, and an inverting input adapted to be coupled to the working electrode of the electrochemical sensing cell, the amplifier further including a feed back element coupled between an output of the amplifier and the inverting input of the amplifier, the feed back element including a resistor and a non-linear element coupled in parallel with the resistor; and wherein the amplifier is powered from the battery.

13. The hazardous gas sensor of claim 12, wherein the non-linear element comprises at least one transistor.

14. The hazardous gas sensor of claim 13, wherein the non-linear element comprises two series connected transistors.

15. The hazardous gas sensor of claim 14, wherein the series connected transistors are configured as voltage followers.

16. The hazardous gas sensor of claim 12, wherein the non-linear element does not conduct when the polarity of the output of the amplifier is negative.

17. The hazardous gas sensor of claim 12, wherein the non-linear element does not conduct below a predetermined voltage across the resistor.

18. The hazardous gas sensor of claim 17, wherein a voltage developed across the resistor provides a linear indication of the concentration of the hazardous gas detected by the electrochemical sensor cell when the non-linear element is not conducting.

19. The hazardous gas sensor of claim 12, wherein the non-linear element begins to conduct at a predetermined voltage across the resistor.

20. The hazardous gas sensor of claim 19, wherein a voltage developed across the resistor no longer provides a linear indication of the concentration of the hazardous gas detected by the electrochemical sensor cell when the non-linear element is conducting, the amplifier instead sourcing current to the working electrode to prevent the electrochemical sensor cell from becoming biased due to a high concentration of the hazardous gas.

* * * * *